United States Patent
Waugh

(10) Patent No.: US 8,658,621 B2
(45) Date of Patent: Feb. 25, 2014

(54) TOPICAL METHOD FOR PROMPT RELIEF OF SEVERE ASCITES

(76) Inventor: William Howard Waugh, Greenville, NC (US)

(*) Notice: Subject to any disclaimer, the term of this patent is extended or adjusted under 35 U.S.C. 154(b) by 356 days.

(21) Appl. No.: 12/658,071

(22) Filed: Feb. 2, 2010

(65) Prior Publication Data

US 2011/0190225 A1   Aug. 4, 2011

(51) Int. Cl.
*C08B 5/02* (2006.01)
*A61K 31/717* (2006.01)

(52) U.S. Cl.
CPC .............. *C08B 5/02* (2013.01); *A61K 31/717* (2013.01)
USPC ............................................. 514/57; 536/35

(58) Field of Classification Search
None
See application file for complete search history.

(56) References Cited

U.S. PATENT DOCUMENTS

2008/0167592 A1* 7/2008 Greer .............................. 602/43

OTHER PUBLICATIONS

"Ascites", Merck Manual Online Edition, [retrieved on Nov. 2, 2011]. Retrieved from the Internet http://www.merckmanuals.com/home/print/. Revision Aug. 2006.*
Arroyo et al., Journal of Hepatology, 2003, 38, S69-S89.*
Altschule, M.D., Physiology in Diseases of the Heart and Lungs revised ed., Harvard University Press, Cambridge, MA, (1954):p. 375.
Angeli P., Merkel C. "Pathogenesis and management of hepatorenal syndrome in patients with cirrhosis". J. Hepatology 48: S93-S103 (2008).
Baggenstoss A.H., Cain J.C., "The hepatic hilar lymphatics of man their relation to ascites". N. Engl.J. Med. 254: 531-535 (1957).
Beers M.H. et al., The Merck Manual of Diagnosis and Therapy 18th ed., Merck Res. Labs. Whitehouse Station, NJ,(2006): a"Laparoscopy" p. 86; b "Ascites" pp. 188-189; c Cirrho.
Belli L., ["New possibilities of influencing surgically the formation of ascites through application of Eastman 910 on the hepatic surface"], L'Ospedale maggiore 58: 647-652.
Belli L. et al., [A new technic for the surgical treatment of ascites . . . Lyon chirugical 61:182-193 (1965).
Belli L., Forti D., [Hepatopexy using tissue adhesives . . . j. Chir. (Paris) 92:589-606 (1966).
Freeman S., "Recent progress in the physiology and biochemistry of the liver". Med. Clin. North America 37: 107-124 (1953).
Garcia-Tsao G., Current management of the complications of cirrhosis and portal hypertension: variceal hemorrhage, ascites . . . Gastroenterology 120:726-748 (2001).
Gines P., Schrier R.W., "Renal failure in cirrhosis" N. Engl. J. Med. 361: 1279-1290 (2009).
Hyatt R.E., Smith J.R., "The mechanism of ascites a physiologic appraisal". Am. J. Med. 13: 434-448 (1954).
Leggat P.A. et al., "Toxicity of cyanoacrylate adhesives and their occupational impacts for dental staff". Ind. Health 42: 207-11 (2004).
Leggat P.A. et al., "Surgical applications of cyanoacylate adhesives: a review of toxicity". ANZ J. Surgery 77: 209-213 (2007).
Lotterhos W.E. et al., "Meeting of the panel on review of miscellaneous external OTC drug products . . . Jan. 29 and30, 1978":—assessed on WWW/internet on Nov. 9, 2009.
Mallet-Guy P. et al.,["Etude Experimentale Des Ascites Stenoses veineuses post-hepatiques et transposition du foie dans le thorax"] Lyon chir (Paris) 49: 153-172 (1954).
Moore K.P. et al., "The management of ascites in cirrhosis: report on the consensus conference of the internal ascites club". Hepatology 38: 258-266 (2003).
Nayak, N.C., "An experimental study of ascites produced after partial ligation of inferior vena cava", Ind. J. Med. Res. 44:403-413 (1956).
Page I.H.,"The production of persistent arterial hypertension by cellophane perinephritis". J. A. M. A. 113:2046-2048 (1939).
Page I.H.,"Demonstration of the liberation of rennin into the blood stream from kidneys of animals made hypertensive by cellophane . . . ". Am. J. Physiol. 130: 22-28 (1940).
Panos M.Z. et al., "Single, total paracentesis for tense ascites: sequential hemodynamic changes . . . " Hepatology 11:662-667 (1990).
Sollmann T., A Manual of Pharmacology fifth ed. W.B. Saunders Co. Philadelphia (1936): p. 140.
Taylor F.W., Rosenbawm D. "The case against hepatic artery ligation in portal hypertension". J.A.M.A. 151: 1066-1969 (1953).
Waugh W.H. "Local factors in the pathogenesis and course of experimental ascites". J. Applied Physiol. 13: 493-500 (1958).
Windholz M. et al. The Merck Index an encyclopedia of chemicals and drugs 9th ed. Merck & Co. Rahway, N. J. (1976): p. 8, p. 31, p. 500-501, or p. 1039.

* cited by examiner

*Primary Examiner* — Eric S Olson
(74) *Attorney, Agent, or Firm* — Lynn E. Barber

(57) ABSTRACT

A means is provided to make the capsules of cirrhotic or fibrotic livers relatively impermeable to liver tissue fluid or lymph in humans or other mammals suffering from severe chronic ascites or refractory ascites by application of collodion. The means will be useful to decrease the need for liver and combined liver and kidney transplantations.

13 Claims, No Drawings

TOPICAL METHOD FOR PROMPT RELIEF OF SEVERE ASCITES

TECHNICAL FIELD

The invention generally relates to systems and methods to reduce ascites caused by post-hepatic and intra-hepatic venous hypertension and by intrinsic liver disease. Specifically, the invention relates to a surgically applied method to relieve promptly severe ascites due to liver disease, in order to decrease the need for liver transplantations and for combined liver and kidney transplantations and to decrease the incidence of spontaneous bacterial peritonitis and renal failure in individuals with cirrhosis.

BACKGROUND OF THE INVENTION AND RELATED ART

Ascites has been known to occur in mankind for many centuries and chronic gross or large-volume ascites due to liver disease has usually been treated by repeated paracenteses, at times followed by colloid volume expansion or insertion of a transjugular intra-hepatic portosystemic stent shunt (Beers et al. 2006: b; Gines, Schrier 2009; Hyatt, Smith 1954; Moore et al. 2003; Panos et al. 1990). Spontaneous bacterial peritonitis is particularly common in cirrhotic ascites, (Beers et al. 2006: b; Gines, Schrier 2009; Garcia-Tsao 2001). In patients with refractory ascites from cirrhosis or who develop the hepatorenal syndrome, the survival prognosis is particularly very poor (Garcio-Tsoa 2001; Angeli, Merkel 2008; Moore et. al. 2003; Gines, Schrier 2009). Indeed, liver transplantation should be considered currently for all cirrhotic patients with gross or refractory ascites before the development of renal dysfunction and with a hepatic venous pressure gradient of 10 mm Hg or higher! (Moore et al. 2003; Gines, Schrier 2009).

Liver cirrhosis is a diffuse fibrotic disease characterized by regenerative nodules surrounded by dense fibrotic tissue (Beers et al. 2006: c). It is presently a leading cause of death world-wide Most cases arise from alcohol abuse or chronic hepatitis C infection in developed countries (Beers et al. 2006: c). Distortions in blood flow to nodules along with compression of hepatic venules contribute to portal hypertension. The surface of the cirrhotic liver is known to be commonly coarsely hob-nail in appearance and the liver size may be hypertrophic or atrophic. Various diseases and drugs cause liver cirrhosis, including those conditions with high venous pressure (intra-hepatic and post-hepatic), which may result from obstructive disease within the post-hepatic inferior vena cava (Budd-Chiari syndrome and in heart failure) (Beers et al. 2006: b, c, d). Heart failure can cause cardiac cirrhosis, including that from adhesive pericarditis in which ascites may be an early developed complication (ascites praecox) from central venous hypertension (Altschule 1954). Ascites and spontaneous bacterial peritonitis are commonly late complications of cirrhosis. Liver transplantation may be a last resort (Beers et al. 2006: c, d). Many patients presently die waiting liver transplants and there are complications from liver transplantations (Beers et al. 2006:e).

Most of the excess peritoneal fluid in cirrhotic ascites has been shown to originate from the liver (Freeman 1953; Mallet-Guy et al. 1954). Upon laparotomy, drops of liver tissue fluid or lymph has been seen to be formed constantly from the liver capsule (Glisson's capsule) (Hyatt, Smith 1954). The liver capsule becomes edematous in the ascites of experimental cirrhosis (Nayak et al. 1956). The hepatic lymphatic vessels are dilated and thickened in cirrhotic humans both with and without ascites (Baggenstross, Cain 1957). The ascites in cirrhosis may disappear spontaneously after several weeks or more in various mammals including man (Hyatt, Smith 1954; Nayak et al. 1956; Waugh 1958). This may occur despite portal and hepatic venous pressures (and sinusoidal pressures) remaining high, or paradoxically even higher than when ascites was present (Waugh 1958). Formerly, it was believed that increased collateral blood circulation developed which reduced pressure gradients and the ascites (Waugh 1958). At autopsy, Waugh observed, 2 and ½ years after canine ascites had disappeared spontaneously, the presence of marked increase in the lymphatic vessels within the superior region of the right dome of the diaphragm, which led from the very cirrhotic liver. Also, impermeability of saline through almost all of the lower regions of the collagenous fibrotic thickened liver capsule was found when saline was infused into the liver through the portal vein at higher hydrostatic pressure than present during life, while the hepatic artery and the vena cava immediately above the liver were both ligated (Waugh 1958). In contrast, the liver capsule of the normal dog was observed to be very thin, friable, and permeable to saline infused into the portal vein at similar pressure with the hepatic artery and vena cava just beyond the normal liver ligated (Waugh 1958).

Topical application of Eastman 910 adhesive diffusely to the surfaces of cirrhotic livers in animals with ascites from congestive cirrhosis resulted in an intensive connective tissue reaction within the liver capsules and incomplete or complete disappearance of the ascites (Belli 1963; Belli et al. 1964). Application of Eastman 910 to the liver capsules was performed as a complimentary procedure in 33 human patients with cirrhosis and ascites after termino-lateral porto-caval anastomoses were done. Reductions or complete resolutions of the ascites resulted in the patients who survived the procedures (Belli et al. 1966). Evaluation of the hepatopexy results with Eastman 910 was difficult because the porto-caval operations had been done just before the adhesive applications. No further studies with Eastman 910 application to humans with cirrhotic ascites apparently have been done since the work of Belli et al. in 1966. The animal and human work of Belli et al. in 1964 and 1966 has been overlooked apparently by medical professionals, surgeons, and gastroenterologists in the past few decades. The work appears to be not well known in the present art (Garcia-Tsao 2001; Moore et al. 2003; Gines, Schrier 2009). Eastman 910 is a cyanoacrylic ester compound which cures by binding in thermal reactions. Toxic reactions have been described with cyanoacrylate adhesives (Leggat et al. 2004; Leggat et al. 2007). By wrapping kidneys in cellophane but avoiding the renal pedicles, Page produced perinephritis with a fibro-collagenous hull and renal hypertension in dogs (Page 1939; Page 1940).

Collodion U.S.P. is a 4 percent solution of nitrocellulose (CAS No: 9004-70-0) (pyroxylin) in a mixture of 3 vols. of ether and 1 vol. of alcohol (Sollmann 1936). It is a syrupy liquid which dries rapidly. It is highly inflammable and should be stored in a cool environment. It is used as a liquid protectant to protect small wounds and it has been used in the absence of toxicity (Sollmann 1936; Lotterhos et al. 1978). It may be purchased in many pharmacies as an over the counter liquid. Collodion U.S.P. is produced by some chemical supply companies, e.g. Mallinckrodt Baker Inc., Philipsburg, N.J. Alternately, collodion liquid of nitrocellulose may be made by dissolving nitrocellulose in acetone (Sollmann 1936; Windholz et al. 1976). The boiling points of diethyl ether, ethyl alcohol, and acetone are, respectively, 34.6, 78.3, and 56.5 degrees Celsius (Windholz et al. 1976). Acetone N.F.and F.C. C. may be obtained at various chemical supply companies.

SUMMARY OF THE INVENTION

The object of the invention is to provide novel means to make promptly the capsules of cirrhotic livers relatively impermeable to liver tissue fluid or lymph in persons suffering from severe chronic ascites or refractory ascites. With such accomplishment, the incidence of spontaneous bacterial peritonitis and the need for repeat paracenteses should decrease. Also, the need for liver transplantations and combined liver and kidney transplantations should be reduced in individuals with chronic liver disease and ascites. To embody the means, a small model was employed which used soft, pliant leather chamois as a test membrane. It was measured for transudation of water at a pressure head of 15 cm. of water (11 mm. Hg). Topical brief application of Collodion U.S.P. or nitrocellulose in acetone, as the collodion liquid, to the inferior surface of the chamois membrane followed by solvent evaporation over the next several minutes at room temperature resulted thereafter in marked reduction of or complete prevention of the permeability of the membrane to water at such high hydrostatic pressure.

DETAILED DESCRIPTION OF THE INVENTION

Collodion in acetone as solvent was prepared by evaporation of the ether and alcohol in aliquots of Collodion U.S.P. at room temperature no higher than 30 degrees Celsius (86 degrees F.) for several hours and then redissolving the residual nitrocellulose to a concentration of 4 percent in acetone.[This solution could be optimally made more syrupy by redissolving the nitrocellulose in less volume of acetone.] As a working small model to measure liquid flux through a membrane at high hydrostatic pressure, transparent vinyl tubing about 40 cm. in length and ½ inch in internal diameter was used. A short hard nylon barb as nozzle of ½ inch internal diameter inserted inside the lower end of the tubing. A sheet of leather chamois covered the lower opening of the tubing nozzle. The chamois was kept tightly in place outside the nylon nozzle by a rubber O-ring, of number 14 and of ¾ inch in its unstretched internal diameter. [Leather chamois may be obtained in textile stores.] The chamois serving as membrane at its lowermost surface had an area of 159 sq. mm. exposed to liquid flux. Outflows of water were collected below this in a small beaker after water was placed into the superior end of the tubing Distilled water was used as the liquid medium. It was poured into the top end of the tubing and membrane outflow was allowed for several minutes before initial measurements of outflux of transudate at 15 cm. water pressure. Before outflux was measured initially and before topical application of collodion to the membrane, the flow of water was stopped by insertion of a number 13 glass stopper into the superior end of the tubing when the water length was about 16 cm. from the chamois membrane. [This maneuver was analogous to hepatic artery ligation for only a brief period in cirrhotic patients with portal hypertension (Taylor, Rosenbaum 1953).] Just before transudate was to be measured, the lower surface of the chamois was gently dried by gauze application. Two "coats" of collodion solution were applied by use of a saturated cotton swab or small paint-brush about 10 min. apart. Solvent evaporation followed each application. [The second application made the thin layer of nitrocellulose thicker and stronger.] Transudates was collected initially for less than 3 seconds immediately after removal of the glass stopper and for a whole one minute period after the second applications of collodion about 12 to 14 min. before. The collected amounts of water were weighed and the transudate rates were converted to ml. per minute at 15 cm. of water head pressure. Four runs were performed with a freshly used chamois membrane each time, both with use of Collodion U.S.P. and with use of the collodion containing acetone as solvent.

Summary of the results are tabulated in the following two EXAMPLES. Transudation of water at 15 cm. hydrostatic pressure averaged 166±13 ml./min. (mean & standard error) before Collodion U.S.P. application. Transudation was inhibited by 99.6±0.2 percent (mean & standard error) afterwards. Before use of nitrocellulose in acetone, the membrane transudate averaged 159±45 ml./min. The transudate rate was inhibited by 97.2±1.5 percent with use of nitrocellulose in acetone.

EXAMPLE 1

| CHAMOIS TRANSUDATE RATES AT PRESSURE OF 15 CM. WATER BEFORE AND AFTER USE OF COLLODION U.S.P. | | |
|---|---|---|
| BEFORE (ml/min) | AFTER (ml/min) | FLUX INHIBITION (percent) |
| 166 ± 13* | 0.33 ± 0.22 * | 99.6 ± 0.2 * $^p$ |

* represents Mean ± SEM of 4 Runs.
$^p$ represents probability <0.001 by paired Student t-test.

EXAMPLE 2

| CHAMOIS TRANSUDATE RATES AT PRESSURE OF 15 CM. WATER BEFORE AND AFTER USE OF COLLODION IN ACETONE * * | | |
|---|---|---|
| BEFORE (ml/min) | AFTER (ml/min) | FLUX INHIBITION (percent) |
| 159 ± 45 * | 1.12 ± 0.6 * | 97.2 ± 1.5 * $^p$ |

* represents Mean ± SEM of 4 runs.
$^p$ represents probability <0.001 by paired Student t-test.
* * nitrocellulose in acetone was used.

The model demonstrations have clinical implications that the topical applications of Collodion U.S.P. and collodion solution as nitrocellulose in acetone, after several minutes of allowed evaporation, are able to prevent soon almost completely transudation of liquid through chamois membranes at pressure gradient of 15 cm. water (11 mm. Hg). This inventor proposes that collodion solution put on to the visible capsular surfaces of cirrhotic livers in mammals suffering from severe chronic ascites or refractory ascites, with evaporation over several minutes, will result soon in attenuation or absence of the ascites. In vivo, complete impermeability to liver fluid transudation at pressure gradient of 11 mm. Hg and higher may result from fibrotic reaction to the film of nitrocellulose in a few days, similar to renal capsule observations after cellophane (Page 1939; Page 1940). To this end, a laparotomy operation, perhaps performed laparoscopically (Beers et al. 2006 a), would be done with syrupy collodion liquid swabbed on to visible surfaces of the liver capsules (Glisson's capsules) with collodion-saturated cotton-swabs or small paint-brushes, with allowed evaporation of the liquid. Optimally, the application of collodion solution would be carried out during brief clamping of the hepatic artery to keep the capsular surfaces relatively dry of liver tissue fluid. Avoidance of application on to the common bile duct, portal vein, and hepatic artery at the hilar region would be recommended. Antecedently, a therapeutic paracentesis likely would be done.

While there has been shown and described what is considered to be preferred embodiments of the invention, it will be understood that various modifications could be made without departing from the scope of the invention. It is intended that the invention be not limited to the exact forms described and illustrated herein, but should be construed to cover modifications that may fall within the scope of the appended claims.

REFERENCES

Altschule, M. D., Physiology In Diseases Of The Heart And Lungs revised ed., Harvard University Press, Cambridge, Mass., (1954):p. 375.
Angeli P., Merkel C. "Pathogenesis and management of hepatorenal syndrome in patients with cirrhosis". J. Hepatology 48: S93-S103 (2008).
Baggenstoss A. H., Cain J. C., "The hepatic hilar lymphatics of man their relation to ascites". N. Engl. J. Med. 254: 531-535 (1957).
Beers M. H. et al., The Merck Manual of Diagnosis and Therapy 18$^{th}$ ed., Merck Res. Labs. Whitehouse Station, N.J., (2006): a "Laparoscopy" p. 86; b "Ascites" pp. 188-189; c "Cirrhosis" pp. 215-219; d "Budd-Chiari syndrome" and "Veno-occlusive disease" pp. 232-234; e "Liver transplantation" pp. 1374-1376.
Belli L., ["New possibilities of influencing surgically the formation of ascites through application of Eastman 910 on the hepatic surface"], L'Ospedale maggiore 58: 647-652 (1963). [Article in Italian]
Belli L. et al., ["A new technic for the surgical treatment of ascites caused by stenosis of the inferior vena cava: hepatopexy by means of adhesives and plasticizing substances"] Lyon chirugical 61: 182-193 (1965).
Belli L., Forti D., ["Hepatopexy using tissue adhesives as a complementary procedure of termino-lateral portocaval anastomosis in the treatment of ascites. (immediate and remote results in 33 operated cases)"] J. Chir. (Paris) 92: 589-606 (1966). [Article in French]
Freeman S., "Recent progress in the physiology and biochemistry of the liver". Med. Clin. North America 37: 107-124 (1953).
Garcia-Tsao G., "Current management of the complications of cirrhosis and portal hypertension: variceal hemorrhage, ascites, and spontaneous bacterial peritonitis". Gastroenterology 120: 726-748 (2001).
Gines P., Schrier R. W., "Renal failure in cirrhosis" N. Engl. J. Med. 361: 1279-1290 (2009).
Hyatt R. E., Smith J. R., "The mechanism of ascites a physiologic appraisal". Am. J. Med. 13: 434-448 (1954).
Leggat P. A. et al., "Toxicity of cyanoacrylate adhesives and their occupational impacts for dental staff". Ind. Health 42: 207-11 (2004).
Leggat P. A. et al., "Surgical applications of cyanoacylate adhesives: a review of toxicity". ANZ J. Surgery 77: 209-213 (2007).
Lotterhos W. E. et al., "Meeting of the panel on review of miscellaneous external OTC drug products twenty-third meeting Jan. 29 and 30, 1978":—assessed on WWW/internet on Nov. 9, (2009).
Mallet-Guy P. et al., ["Etude Experimentale Des Ascites Stenoses veineuses post-hepatiques et transposition du foie dans le thorax"] Lyon chir (Paris) 49: 153-172 (1954). [Article in French]
Moore K. P. et al., "The management of ascites in cirrhosis: report on the consensus conference of the internal ascites club". Hepatology 38: 258-266 (2003).
Nayak N. C. et al., "An experimental study of ascites produced after partial ligation of inferior vena cava". Indian J. Med. Res. 44: 403-413 (1956).
Page I. H., "The production of persistent arterial hypertension by cellophane perinephritis". J. A. M. A. 113:2046-2048 (1939).
Page I. H., "Demonstration of the liberation of rennin into the blood stream from kidneys of animals made hypertensive by cellophane perinephritis". Am. J. Physiol. 130: 22-28 (1940).
Panos M. Z. et al., "Single, total paracentesis for tense ascites: sequential hemodynamic changes and right atrial size". Hepatology 11: 662-667 (1990).
Sollmann T., A Manual of Pharmacology fifth ed. W.B. Saunders Co. Philadelphia (1936): p. 140.
Taylor F. W., Rosenbawm D. "The case against hepatic artery ligation in portal hypertension". J.A.M.A. 151: 1066-1969 (1953).
Waugh W. H. "Local factors in the pathogenesis and course of experimental ascites". J. Applied Physiol. 13: 493-500 (1958).
Windhholz M. et al. The Merck Index an encyclopedia of chemicals and drugs 9$^{th}$ ed. Merck & Co. Rahway, N.J. (1976): p. 8, p. 31, p. 500-501, or p. 1039.

What is claimed is:

1. A method of lessening ascites due to liver disease in a subject, comprising applying liquid collodion to the liver capsule of the subject during a laparotomy procedure.

2. The method according to method 1, wherein Collodion U.S.P. is applied topically to the exposed surfaces of the liver capsule during the laparotomy procedure with evaporation of solvent before completion of the laparotomy operation in a subject.

3. The method according to method 1, wherein collodion solution consisting of nitrocellulose in acetone is applied topically to the exposed surfaces of the liver capsule during the laparotomy procedure with evaporation of solvent before completion of the laparotomy operation in a subject.

4. The method according to method 1, wherein the subject is a human.

5. The method according to method 1, wherein the subject is a non-human mammal.

6. The method according to method 1, wherein the subject has refractory ascites.

7. The method according to method 1, wherein the subject has tense ascites.

8. The method according to method 1, wherein the subject has had a spontaneous bacterial peritonitis history as a complication of cirrhotic ascites.

9. The method according to method 1, wherein the subject is being considered for liver transplantation.

10. The method according to method 1, wherein the subject has the hepato-renal syndrome as a complication of cirrhotic ascites.

11. The method according to method 1, wherein the subject is being considered for combined liver and kidney transplantations.

12. The method according to method 1, wherein the subject has congestive-type cirrhotic ascites in the Budd-Chiari syndrome.

13. The method according to method 1, wherein the subject has congestive-type cirrhotic ascites due to heart failure.

* * * * *